United States Patent
Dabrowiak

(10) Patent No.: US 9,662,243 B2
(45) Date of Patent: May 30, 2017

(54) HEAT EXCHANGE CATHETERS WITH BI-DIRECTIONAL FLUID FLOW AND THEIR METHODS OF MANUFACTURE AND USE

(71) Applicant: Zoll Circulation, Inc., Sunnyvale, CA (US)

(72) Inventor: Jeremy Thomas Dabrowiak, Redwood City, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 149 days.

(21) Appl. No.: 13/631,076

(22) Filed: Sep. 28, 2012

(65) Prior Publication Data
US 2013/0178923 A1   Jul. 11, 2013

Related U.S. Application Data

(60) Provisional application No. 61/542,024, filed on Sep. 30, 2011.

(51) Int. Cl.
*A61F 7/12* (2006.01)
*A61F 7/00* (2006.01)

(52) U.S. Cl.
CPC .......... *A61F 7/12* (2013.01); *A61F 2007/0054* (2013.01); *A61F 2007/126* (2013.01)

(58) Field of Classification Search
CPC ....... A61F 7/12; A61F 2007/126; A61F 7/123
USPC ........................................... 128/898
See application file for complete search history.

(56) References Cited

U.S. PATENT DOCUMENTS

| | | | |
|---|---|---|---|
| 4,298,006 A * | 11/1981 | Parks | ............ 607/106 |
| 5,837,003 A | 11/1998 | Ginsburg | |
| 5,931,848 A * | 8/1999 | Saadat | ............ 606/167 |
| 6,019,783 A | 2/2000 | Philips et al. | |
| 6,126,684 A | 10/2000 | Gobin et al. | |
| 6,146,411 A | 11/2000 | Noda et al. | |

(Continued)

FOREIGN PATENT DOCUMENTS

| WO | WO99/52455 A1 | 10/1999 |
|---|---|---|
| WO | WO99/66970 A1 | 12/1999 |
| WO | WO00/32126 A1 | 6/2000 |

OTHER PUBLICATIONS

Supplementary Search Report dated May 20, 2015 for corresponding European Patent Application 12836409.8.

(Continued)

*Primary Examiner* — Linda Dvorak
*Assistant Examiner* — Yasamin Ekrami
(74) *Attorney, Agent, or Firm* — Robert D. Buyan; Stout, Uxa & Buyan, LLP

(57) ABSTRACT

Closed loop heat exchange catheters having bi-directional flow heat exchange regions and their methods of manufacture and use. The heat exchange region may be formed of expandable or non-expandable tubular conduit(s) that are configured in a series of loops or coiled configuration defining a supply flow path and a return flow path through which heat exchange medium is circulated. The individual loops of convolutions of the coiled configuration may be the same or different size. In some embodiments, the tubular conduit(s) may be passed through generally transverse bore holes formed in a catheter shaft so that the loops or convolutions of protrude from the catheter shaft.

18 Claims, 7 Drawing Sheets

(56) References Cited

U.S. PATENT DOCUMENTS

| | | |
|---|---|---|
| 6,299,599 B1 | 10/2001 | Pham et al. |
| 6,338,727 B1 | 1/2002 | Noda et al. |
| 6,368,304 B1 | 4/2002 | Aliberto et al. |
| 6,451,045 B1* | 9/2002 | Walker et al. .............. 607/105 |
| 6,551,349 B2 | 4/2003 | Lasheras et al. |
| 6,554,797 B1 | 4/2003 | Worthen |
| 6,581,403 B2 | 6/2003 | Whitebook et al. |
| 6,585,692 B1 | 7/2003 | Worthen |
| 6,589,271 B1 | 7/2003 | Tzeng et al. |
| 6,673,042 B1* | 1/2004 | Samson et al. .............. 604/104 |
| 6,679,907 B2* | 1/2004 | Dobak et al. .............. 607/105 |
| 6,695,873 B2* | 2/2004 | Dobak et al. .............. 607/105 |
| 6,706,060 B2* | 3/2004 | Tzeng et al. .............. 607/105 |
| 6,749,625 B2 | 6/2004 | Pompa et al. |
| 6,796,995 B2 | 9/2004 | Pham et al. |
| 6,881,551 B2 | 4/2005 | Heller et al. |
| 7,287,398 B2 | 10/2007 | Noda et al. |
| 7,857,781 B2 | 12/2010 | Noda et al. |
| 2001/0016764 A1 | 8/2001 | Dobak |
| 2002/0045925 A1* | 4/2002 | Keller .................... A61F 7/12 607/106 |
| 2002/0116039 A1 | 8/2002 | Walker et al. |
| 2002/0183816 A1* | 12/2002 | Tzeng .................... A61F 7/12 607/105 |
| 2002/0193738 A1 | 12/2002 | Adzich et al. |
| 2004/0044387 A1* | 3/2004 | Pompa .................... A61F 7/12 607/105 |
| 2004/0106969 A1 | 6/2004 | Dobak, III et al. |
| 2004/0111138 A1* | 6/2004 | Bleam .................... A61F 7/12 607/105 |
| 2005/0010273 A1 | 1/2005 | Walker et al. |
| 2005/0076924 A1* | 4/2005 | Dobak, III .............. A61B 18/02 128/898 |
| 2008/0071337 A1 | 3/2008 | Dobak, III et al. |
| 2009/0247963 A1* | 10/2009 | Bleam et al. ................. 604/246 |
| 2011/0106051 A1 | 5/2011 | Saab |

OTHER PUBLICATIONS

International Search Report and Written Opinion for corresponding PCT/US2012/057970. International filing date Sep. 28, 2012.
Office Action Dated May 17, 2016 in corresponding Japanese Patent Application No. 2014-533409.

* cited by examiner

HEAT EXCHANGE CATHETERS WITH BI-DIRECTIONAL FLUID FLOW AND THEIR METHODS OF MANUFACTURE AND USE

RELATED APPLICATION

This patent application claims priority to U.S. Provisional Patent Application No. 61/542,024 filed Sep. 30, 2011, the entire disclosure of which is expressly incorporated herein by reference.

FIELD OF THE INVENTION

The present invention relates to medicine and biomedical engineering and more particularly to heat exchange catheter devices and their methods of manufacture and use.

BACKGROUND OF THE INVENTION

Pursuant to 37 CFR 1.71(e), this patent document contains material which is subject to copyright protection. The copyright owner has no objection to facsimile reproduction of the entire patent document or the patent disclosure, as it appears in the Patent and Trademark Office patent file or records, but otherwise reserves all copyright rights whatsoever.

Hypothermia can be induced in humans and some animals for the purpose of protecting various organs and tissues (e.g., hear, brain, kidneys) against the effects of ischemic, anoxic or toxic insult. For example, animal studies and/or clinical trials suggest that mild hypothermia can have neuroprotective and/or cardioprotective effects in animals or humans who suffer from ischemic cardiac events (e.g., myocardial infract, acute coronary syndromes, etc.), postanoxic coma after cardiopulmonary resuscitation, traumatic brain injury, stroke, subarachnoid hemorrhage, fever and neurological injury. Also, studies have shown that whole body hypothermia can ameliorate the toxic effects of radiographic contrast media on the kidneys (e.g., radiocontrast nephropathy) of patients with pre-existing renal impairment who undergo angiography procedures.

One method for inducing hypothermia is by endovascular temperature management (ETM) wherein a heat exchange catheter is inserted into a blood vessel and a thermal exchange fluid is circulated through a heat exchanger positioned on the portion of the catheter that is inserted in the blood vessel. As the thermal exchange fluid circulates through the catheter's heat exchanger, it exchanges heat with blood flowing past the heat exchange in the blood vessel. Such technique can be used to cool the subject's flowing blood thereby resulting in a lowering of the subject's core body temperature to some desired target temperature. ETM is also capable of warming the body and/or of controlling body temperature to maintain a monitored body temperature at some selected temperature. If a controlled rate of re-warming or re-cooling from the selected target temperature is desired, that too can be accomplished by carefully controlling the amount of heat added or removed from the body and thereby controlling the temperature change of the patient.

In most if not all commercially available heat exchange catheters, the heat exchange fluid flows through an inflow lumen of the catheter shaft, then enters one end of the catheter's heat exchanger, then flows through the heat exchanger, then exits from the heat exchanger into an outflow lumen located within the catheter shaft. In general, greater heat exchange efficiency is accomplished when the heat exchange fluid flows through the catheter's heat exchanger in a direction that is opposite the direction in which the blood is flowing through the blood vessel in which the heat exchanger is positioned. Thus, the type of catheter used and/or the selection of which port(s) of the catheter should be used for inflow and outflow, respectively, is sometimes dictated by the intended sites of entry and positioning of the catheter. For example, in some cases, a heat exchange catheter is inserted into a femoral vein and advanced to a position where its heat exchanger is within the subject's vena cava. In such cases, the blood flowing normally through the vena cava will progress from the proximal end of the heat exchanger toward the distal end of the heat exchanger. Thus, in those cases, it will generally be desirable for the heat exchange fluid to enter the catheter's heat exchanger at its distal end and flow back toward the proximal end of the heat exchanger (i.e., counter to the direction of blood flow). If, however, the heat exchanger catheter were inserted into a femoral artery and advanced to a position where its heat exchanger is within the descending aorta, blood flowing normally through the descending aorta would progress from the distal end of the heat exchanger toward the proximal end of the heat exchanger. Thus, in those cases, it would generally be desirable for the heat exchange fluid to enter the catheter's heat exchanger at its proximal end and flow distally toward the distal end of the heat exchanger (i.e., again counter to the direction of blood flow).

Also, in heat exchange catheters where the heat exchange fluid flows in only a single direction through the catheter's heat exchanger, the heat exchange fluid typically is shunted to one or the other end of the heat exchanger through an internal lumen of the catheter. While traveling though that internal lumen the heat exchange fluid is exchanging only minimal if any heat with the flowing blood.

The following U.S. patents, the entire disclosures of which are expressly incorporated herein by reference, disclose various intravascular catheters/systems/methods useable for altering or maintaining a subject's body temperature: U.S. Pat. Nos. 6,881,551 and 6,585,692 (tri-lobe catheter), U.S. Pat. Nos. 6,551,349 and 6,554,797 (metal catheter with bellows), U.S. Pat. Nos. 6,749,625 and 6,796,995 (catheters with non-straight, non-helical heat exchange elements), U.S. Pat. Nos. 6,126,684, 6,299,599, 6,368,304, and 6,338,727 (catheters with multiple heat exchange balloons), U.S. Pat. Nos. 6,146,411, 6,019,783, 6,581,403, 7,287,398, and 5,837,003 (heat exchange systems for catheter), U.S. Pat. No. 7,857,781 (various heat exchange catheters).

There remains a need in the art for the development of new heat exchanger catheters and methods which offer improved heat exchange efficiency and/or ease of use.

SUMMARY OF THE INVENTIONS

In accordance with the present invention, there are provided heat exchange catheter devices having bi-directional flow of heat exchange fluid though a heat exchange region of the catheter.

Further in accordance with the present invention, there are provided methods for modifying or controlling a body temperature of a human or animal subject by inserting a bi-directional flow heat exchange catheter of the present invention and circulating heat exchange medium through the catheter to bring about the desired modification of control of a body temperature of the subject. In some embodiments the catheter may comprise a catheter shaft and tubular conduit(s) that is/are arranged on or connected to the catheter shaft to define a heat exchange region having a heat exchange medium supply flow path and a heat exchange medium return flow path. As explained in detail herein, the tubular conduit(s) may be passed (e.g., laced) through bores in the catheter shaft such that loops of the tubular conduit(s) protrude from the catheter shaft or they may be attached to but positioned entirely outboard of the catheter shaft. The tubular conduit(s) may be formed of non-expanding tubing or, in some embodiments, the tubular conduit(s) may comprise balloons or collapsible tubing (e.g., compliant or non-compliant material) that alternately expands and collapses in accordance with the pressure of heat exchange medium currently within the tubular conduit(s).

Still further aspects and details of the present invention will be understood upon reading of the detailed description and examples set forth herebelow.

DETAILED DESCRIPTION OF THE INVENTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

In typical heat exchange catheter systems of the prior art, a heat exchange medium (e.g., heated or cooled saline solution) is circulated though a heat exchanger located on a flexible heat exchange catheter while the catheter is inserted within a blood vessel of the subject whose body temperature is to be warmed, cooled or maintained. Typically, the heat exchange fluid flows in one direction through the catheter's heat exchanger (i.e., either the distal (outbound) direction or the proximal (inbound) direction. This results in either co-current or counter-current heat exchange, respectively. In co-current heat exchange, the heat exchange fluid is flowing through the catheter's heat exchanger in the same direction as the subject's blood is flowing past the heat exchanger. In counter-current heat exchange, the heat exchange fluid is flowing through the catheter's heat exchanger in a direction that is opposite the direction in which the subject's blood is flowing past the heat exchanger. The present invention provides heat exchange catheters and systems wherein the catheter's heat exchanger has both a distal (i.e., outbound) flow path and a proximal (i.e., inbound) flow path so that heat exchange fluid flows through the catheter's heat exchanger in both co-current and counter-current fashion. As explained more fully herebelow, this bi-directions flow of heat exchange fluid through the catheter's heat exchanger minimizes the time the heat exchange fluid spends within the catheter shaft and maximizes the time in which the heat exchange fluid is flowing through the catheter's heat exchanger and effectively exchanging heat with the subject's blood. Additionally, this bi-directional flow of heat exchange fluid allows the heat exchange fluid to enter and exit the same end (e.g., the proximal end) of the catheter's heat exchanger, thereby avoiding any need to provide a distal lumen to shuttle heat exchange fluid through the catheter shaft to or from the distal end of the heat exchanger. This allows for use of a catheter shaft that is relatively thick walled which does not support high heat transfer rates and also allows for the inflow and outflow lumens in the proximal catheter shaft to be shorter in length. Compared to the heat exchange tube, the inflow and outflow lumens are relatively small in diameter. Therefore, shortening their length will reduce the amount of pressure required to drive saline through the catheter, and/or increase the rate of saline flow thereby increasing the rate of heat exchange.

Figure 1:
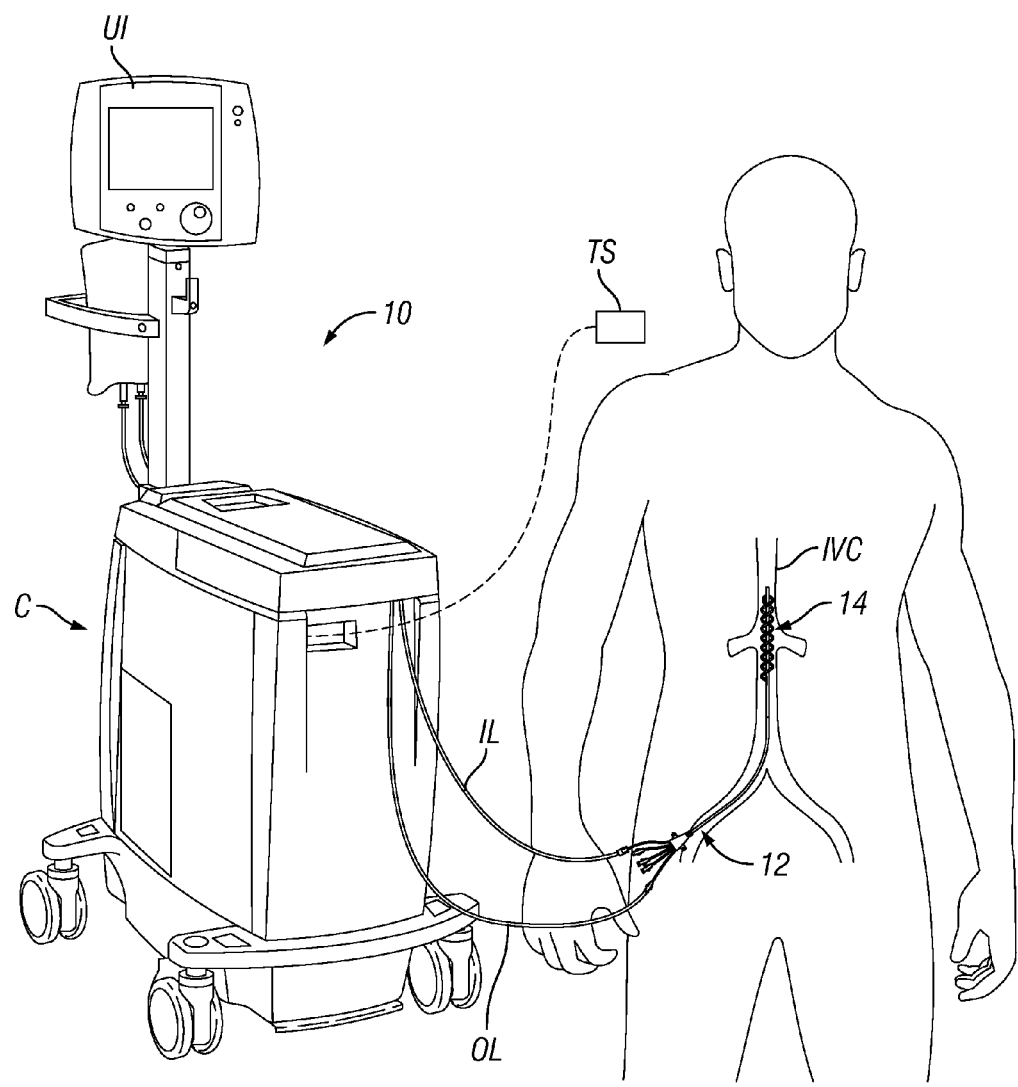
FIG. 1 is a schematic diagram of an endovascular temperature management system of the present invention.

FIG. 1 is a schematic diagram of an endovascular temperature management system 10 which comprises a heat exchange catheter 12 of a type having heat exchange tubing loops 14, an extracorporeal control console C and at least one body temperature sensor TS. In this example, the extracorporeal console C contains a controller (e.g., a microprocessor controller), a user interface UI for inputting data to the controller, a heater/cooler for adjusting the temperature of a thermal exchange medium (e.g., 0.9% sodium chloride solution) and a pump for pumping the thermal exchange medium.

The catheter 12 is connected to the extracorporeal console C by way of an inflow line IL and an outflow line OL so that the pump within the console C will circulate temperature-controlled thermal exchange medium through a heat exchange tube 14 that is mounted or laced onto the catheter such that a first segment of the heat exchange tube runs in the distal (outbound) direction and a second segment of the tube 14 returns in the proximal (inbound) direction. As shown, the heat exchange tube 14 may be configured in a series of loops that protrude outwardly from the catheter body so that the flowing through the subject's vasculature will pass over and in proximity with the heat exchange tubing 14, thereby allowing heat to be exchanged between the circulating thermal exchange medium and the subject's flowing blood. Warming or cooling of the subject's flowing blood then results in warming or cooling of all or a desired portion of the subject's body. In the particular non-limiting example shown in FIG. 1, the distal portion of the catheter 12 is positioned so that the heat exchange tubing loops 14 reside within the subject's inferior vena cava IVC, such catheter positioning being suitable for applications wherein whole body temperature management is desired.

The temperature sensor(s) TS may be positioned on or in the subject's body to measure the temperature of all or part of the body where it is desired to effect temperature modification or control. The controller within the console C receives signals from the temperature sensor(s) TS indicating the currently sensed body temperature. A desired target temperature may be input via the user interface UI and the controller will then issue control signals to the heater cooler and/or pump to adjust the temperature and/or the flowate of the heat exchange medium in an effort to attain and/or maintain the target body temperature. A control console of the type shown in FIG. 1 and described in this example is commercially available as the Thermogard XP™ Temperature Management System from ZOLL Circulation of Sunnyvale, Calif.

The catheter 12 of this example may be constructed and manufactured in the manner shown in FIGS. 2A through 4. In this example, the catheter 12 generally comprises an elongate catheter body 11 and a heat exchange tube 14. The catheter body 11 has at least an inflow lumen 18 and an outflow lumen 19 which extend through at least a proximal portion of the catheter body 11. Optionally, in any catheter of the present invention, a through lumen 16 may extend through the entire length of the catheter body 11, terminating distally in an opening in the distal end of the catheter 12 so as to be useable as a distal infusion or guidewire lumen. Also, optionally, in any catheter of the present invention, the catheter body may include one or more additional lumens and ports, such as an optional medial infusion lumen (not shown) terminating in a medial infusion port (item 46 on FIG. 4) and/or a proximal infusion lumen (not shown) terminating in a proximal infusion port (item 44 on FIG. 4). The individual lumens of the catheter 12 may be integrally formed (e.g., extruded) within the catheter body 11 or may comprise one or more separate tube(s) that are passed through a lumen of the catheter body 11.

Figure 2A:
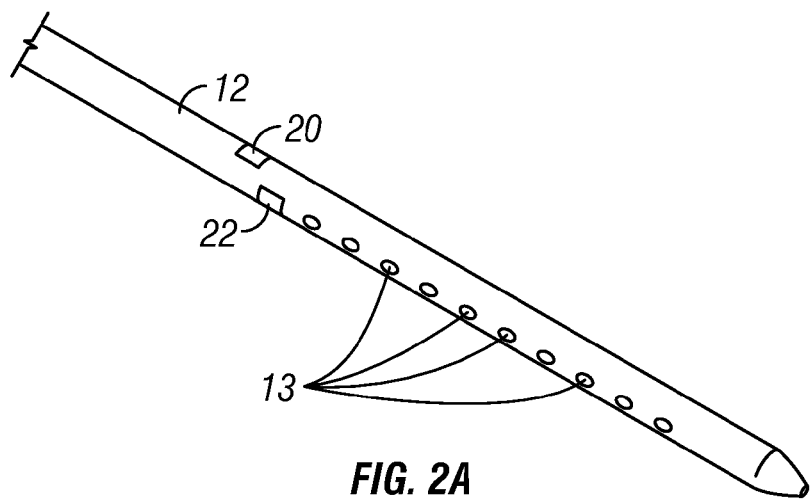
FIG. 2A is a partial perspective view of a portion of a catheter body having a plurality of transverse bores formed therein during manufacture of a catheter device of the present invention.

As seen in FIG. 2A, at the time of manufacture, a series of transverse bores 13 are formed through the catheter body 12. These transverse bores 13 may be formed at any suitable angle relative to the longitudinal axis LA of the catheter body 11. Also, a first window 20 leading into the inflow lumen 18 is skived or otherwise formed at a first location in a wall of the catheter body 11, at a location that is proximal to the bores 13. A second window 22 leading into the outflow lumen 19 is skived or otherwise formed at a second location in a wall of the catheter body 11, also proximal to the bores 13.

Figure 2B:
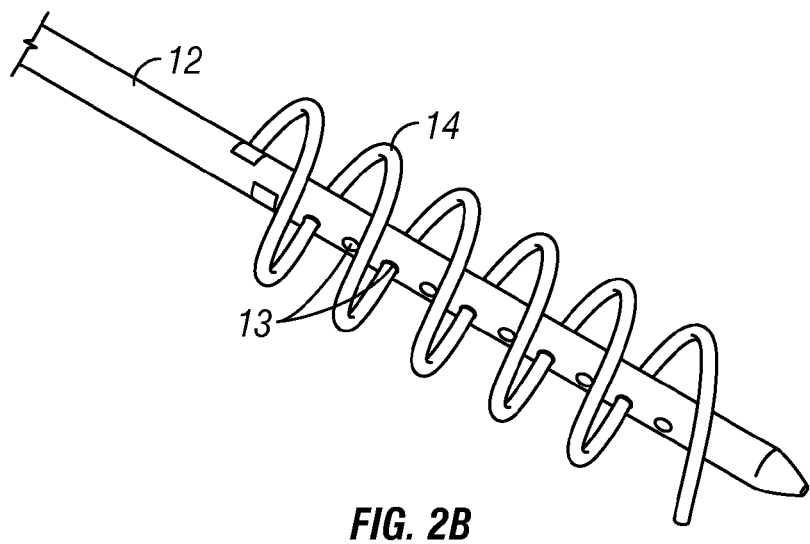
FIG. 2B is a partial perspective view of the catheter body portion of FIG. 2 having a tube passed in alternating directions through the transverse bores such that loops of the tube protrude on opposite sides of the catheter thereby forming a supply flow path for heat exchange fluid.

As shown in FIG. 2B, a first (outbound) segment of the heat exchange tube 14 is advanced toward the distal end of the catheter 12 traversing through though every other bore 13 such that loops of that first segment of the heat exchange tube 14 remain protruding outboard of the catheter body 11.

Figure 2C:
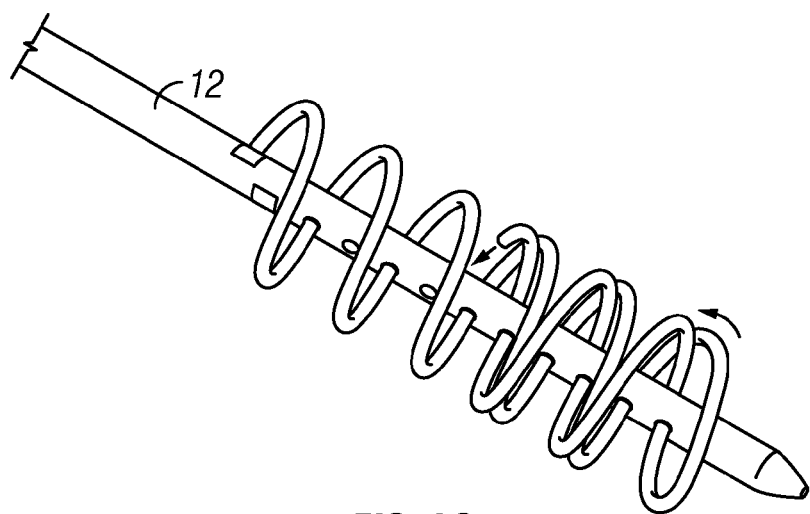
FIG. 2C shows the catheter body of FIG. 2B with the tube being further passed in alternating directions through intervening transverse bores such that additional loops of the tube protrude on opposite sides of the catheter thereby forming a return flow path for heat exchange fluid.
Figure 2D:
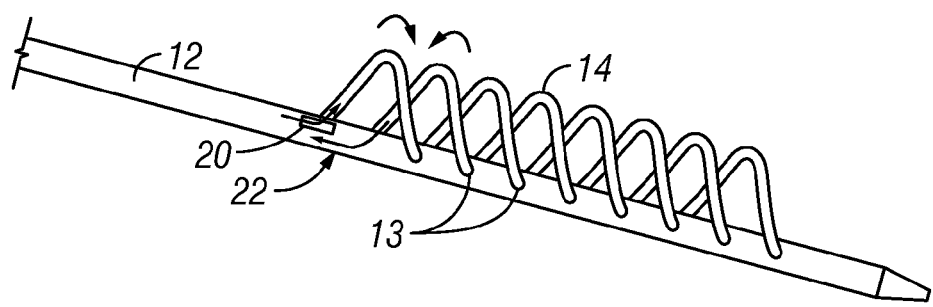
FIG. 2D is a partial perspective view of one example of a bi-directional flow heat exchange catheter of the present invention.
Figure 2E:
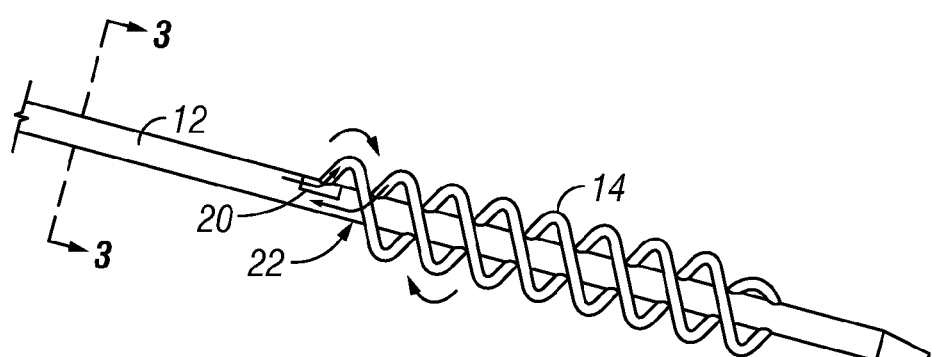
FIG. 2E is a partial perspective view of another example of a bi-directional flow heat exchange catheter of the present invention.
Figure 3:
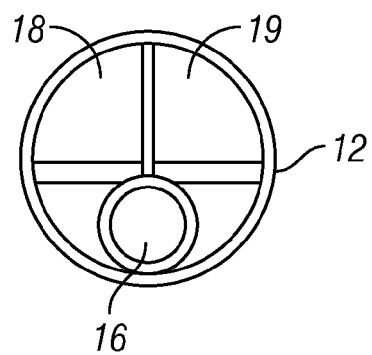
FIG. 3 is a transverse cross sectional view through line 3-3 of FIG. 2E3.

Thereafter, as seen in FIG. 2C, a second (inbound) segment of the heat exchange tube 14 is advanced back toward the proximal end of the catheter 12, traversing through the remaining bores 13, thereby forming loops in that second segment of the tube 14, as shown. It is to be appreciated that the manner in which the tube 14 is laced, threaded or otherwise disposed may vary. As discussed more fully below, FIGS. 8A through 8G show examples of alternative ways in which the tube 14 may be laced, threaded or otherwise disposed and/or other alternative modes for construction of bi-directional flow catheters of the present invention.

A first end of the heat exchange tube 14 is inserted through window 20 into inflow lumen 18 and secured to the wall of the inflow lumen 18. This forms a sealed connection through which inflowing thermal exchange medium will flow from the inflow lumen 18 into the first (e.g., distal) end of the heat exchange tube 14. Sealing attachment of the heat exchange tube 14 to the luminal wall of the inflow lumen 18 may be accomplished by any suitable means such as heat sealing or by adhesive bonding. Examples of adhesives that are useable for this purpose include but are not necessarily limited to cyanoacrylate adhesives (e.g. Loctite 4011 available from the Henkel Corporate, Westlake, Ohio, UV curing acrylic adhesives (e.g. Loctite 3311 available from Henkel Corporate, Westlake, Ohio, and epoxy adhesives (e.g. Loctite 3981 available from Henkel Corporate, Westlake, Ohio). The other end of the heat exchange tube 14 is inserted through window 22 into outflow lumen 19 and secured to the wall of the outflow lumen 19 in the same manner as described above.

This construction allows thermal exchange medium to flow into the catheter 12 through the inflow lumen 18, then into the first end of the heat exchange tube 14, through the first segment of the heat exchange tube (in the distal direction), then back through the second segment of the heat exchange tube 14 (in the proximal direction), into the outflow lumen 19 and then out of the catheter 12. In this manner, thermal exchange medium flows through the heat exchange tube in both the distal direction and proximal directions.

In the particular example shown, the bores 13 are oval or ovoid shaped bores formed by advancing an oval or ovoid shaped punch through the catheter body 12 on a predetermined trajectory or by suitable alternative means such as laser cutting or water jet cutting. Such bores 13 extend through the catheter body 12 substantially at right angles relative to the longitudinal axis LA of the catheter body 12. The trajectory of the bores 13 will avoid obliteration of the through lumen 16 such that the wall of that lumen 16 remains in tact. In embodiments that have optional lumens in the proximal portion of the catheter body 11 (e.g., a proximal and/or medial infusion lumen), such proximal lumens may terminate or be terminally sealed to proximal and medial infusion lumen outlet openings 44, 46 (seen on FIG. 4) at locations proximal to where the bores 13 are formed. Therefore, the optional medial and proximal infusion lumens (if present) are nonfunctional in the region where the bores 13 are formed.

The catheter body 11 may be appropriately sized and formed of any material(s) suitable for the intended applications of the catheter device. For example, in many applications, it will be desirable for the catheter body 12 to have enough rigidity and wall thickness to contain working pressures of up to about 100 psi while being sufficiently flexible to navigate through the intended blood vessels or other body lumens to the desired location within a subject's body. Typically, this may be accomplished by a catheter body that has an outer diameter of 6 Fr (0.080") to 14 Fr (0.180") and is formed of a biocompatible polyurethane (e.g., Elastollan™ available from BASF Corporation, Florham Park, N.J. or Tecothane™ available from The Lubrizol Corporation, Wickliffe, Ohio) or polyether block amide (e.g., Pebax™ available from Arkema, Inc., Philadelphia, Pa.).

The heat exchange tube 14 may be appropriately sized and formed of any material(s) suitable for the intended applications of the catheter device. For example, in many applications, it will be desirable for the heat exchange tube 14 to a) have a thin wall thickness (typically around 0.001") to best facilitate heat transfer, b) have sufficient tensile strength to withstand pressures of up to about 100 psi and c) be sufficiently rigid or semi-rigid so as not to expand uncontrollably under pressure. Thus, it will be desirable for the tube 14 to be formed of a material capable of being extruded and/or blown into a tube having such wall thickness and properties. Examples of materials that may be suitable for forming the tube 14 include polyethylene terephthalates (PETs) available from a variety of sources or polyether block amide (e.g., Pebax™ available from Arkema, Inc., Philadelphia, Pa.).

In some embodiments, it will be desirable to form the protruding loops of heat exchange tube 14 into desired shapes by thermosetting or other suitable forming techniques.

Figure 4:
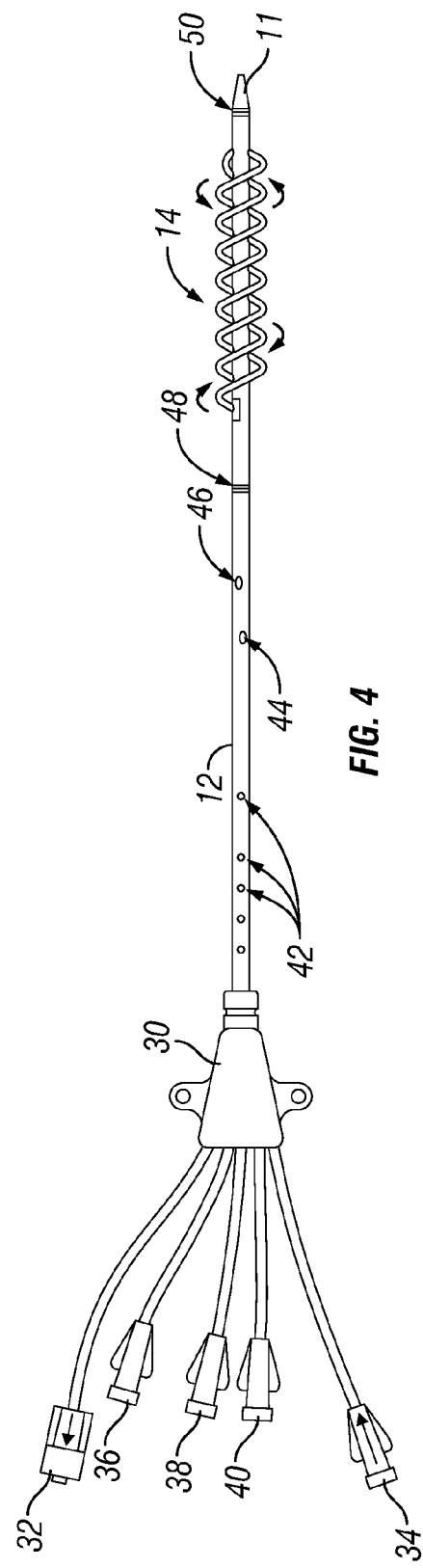
FIG. 4 is a side view of one embodiment of a fully assembled catheter device of the present invention having a heat exchange region as shown in FIG. 2E.

Also, as shown in FIG. 4, when fully assembled, the catheter device 12 of this example includes a hub 30 on its proximal end, with an outflow lumen connector 32 (connected to outflow lumen 19), inflow lumen connector 34 (connected to inflow lumen 18), optional medial infusion lumen connector 36 (connected to an optional medial infusion lumen), through lumen connector 36 (connected to the through lumen 16 useable as a distal infusion or guidewire lumen) and an optional proximal infusion lumen connector 36 (connected to an optional proximal infusion lumen).

Additionally, graduated distance markings 42 may optionally be formed on a proximal region of the catheter body 11 to indicate the length of catheter that is indwelling in the body at any particular time. Also, an optional proximal radiographic marker 48 and an optional distal radiographic marker 50 are located on the catheter body to facilitate radiographic determination of the location of the heat exchanging region (e.g., the protruding tube loops 14) within a subject's body.

Figure 5:
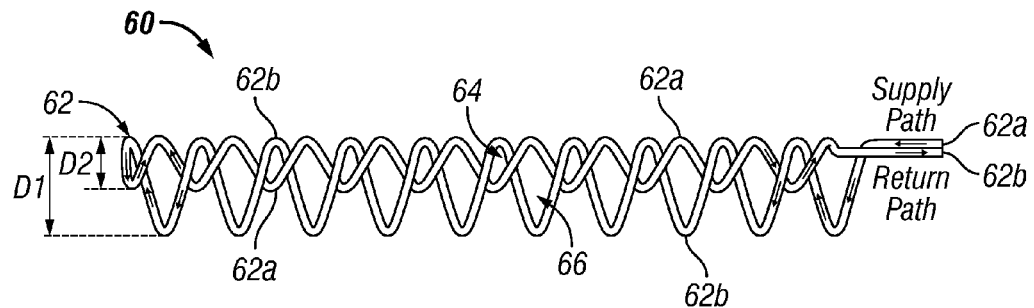
FIG. 5 is a side view of an alternative bi-directional flow heat exchange device useable on heat exchange catheters of the present invention, wherein the heat exchange fluid return flow path is shorter than the heat exchange fluid supply flow path.
Figure 6:
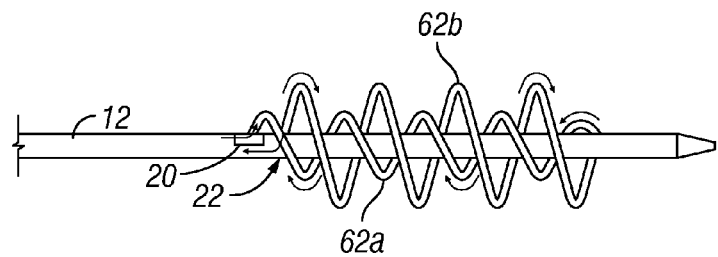
FIG. 6 is a partial side view of yet another example of a bi-directional flow heat exchange catheter of the present invention, in which the heat exchange region has a heat exchange fluid return flow path that is shorter than the heat exchange fluid supply flow path.
Figure 7:
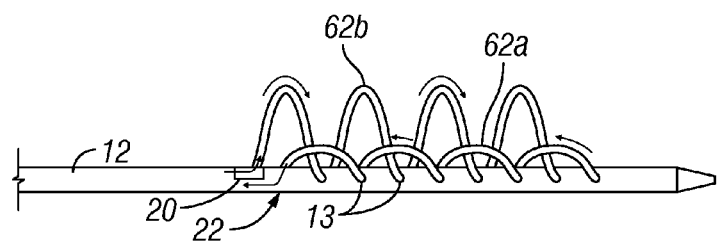
FIG. 7 is a partial side view of yet another example of a bi-directional flow heat exchange catheter of the present invention, in which the heat exchange region has a heat exchange fluid return flow path that is shorter than the heat exchange fluid supply flow path.

FIGS. 5 through 7 show an alternative embodiment wherein the heat exchange region 60 comprises a tubular conduit 62 that is arranged in a first series of loops 66 of diameter or cross-dimension D1 forming the heat exchange fluid supply path 62a and a returning second series of loops 64 of diameter or cross-dimension D2 forming the return flow path 62b. D2 is smaller than D1. Thus, in this embodiment, the return flow path 62b is configured to be radially smaller than the supply flow path 62a. Also, in this embodiment, the overall length of the tubular conduit that forms the return flow path 62b is shorter than that which forms the supply flow path 62a.

Providing a return flow path 62b that is radially smaller and/or shorter in overall tubular conduit length than the supply flow path 62a has been found to substantially increase heat exchange efficiency with blood or body fluid that flows in heat exchange proximity to the heat exchange region 60.

The portion of the tubular conduit forming the supply flow path 62a receives heat exchange fluid from the inflow lumen of the catheter shaft. The heat exchange fluid then flows from the proximal end of the through the coiled supply flow path 62a to its distal end, where it then circulates into the distal end of the tubular conduit that forms the return flow path 62b and then returns in the proximal direction through return flow path 62b. The return flow path is connected to the return lumen of the catheter shaft such that the returning heat exchange fluid will circulate back to the extracorporeal portions of the system as described above. The supply and return conduits 62a, 62b of this heat exchange region 60 may be spaced from each other except at the distal location, such that blood can flow between and around the surfaces of the conduits when the catheter is positioned in a blood vessel of a subject.

Figure 5A:
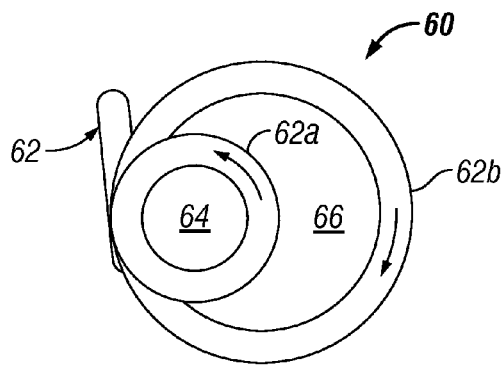
FIG. 5A is a distal end view of the alternative bi-directional flow heat exchange device of FIG. 5.

The loops or other convolutions 64, 66 of the supply and return flow paths 62a, 62b may or may not be coaxial and they may be of various shapes other than the round shape shown in FIGS. 5 and 5A. For example, FIGS. 6 and 7 show examples of bi-directional flow heat exchange catheters that are similar in construction and design to those shown in FIGS. 2D and 2E, but wherein the tubular conduit that forms the return flow path 62a is arranged in loops that are smaller in cross-dimension than those of the supply flow path 62a.

Figure 8A:
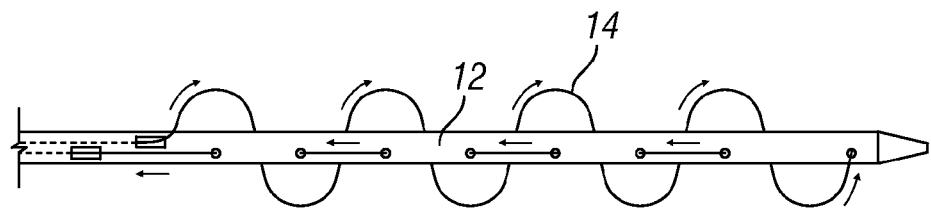
FIGS. 8A through 8G are schematic diagrams that show various alternative ways in which tubing may be deployed on and/or in catheters of the present invention to form heat exchange regions having bi-directional heat exchange fluid flow paths.
Figure 8B:
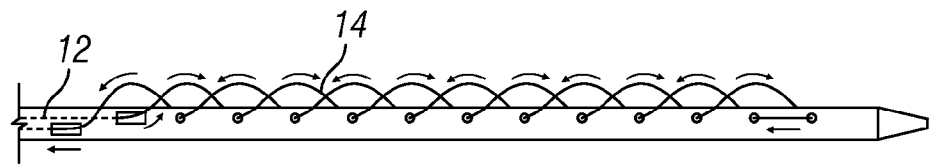
Figure 8C:
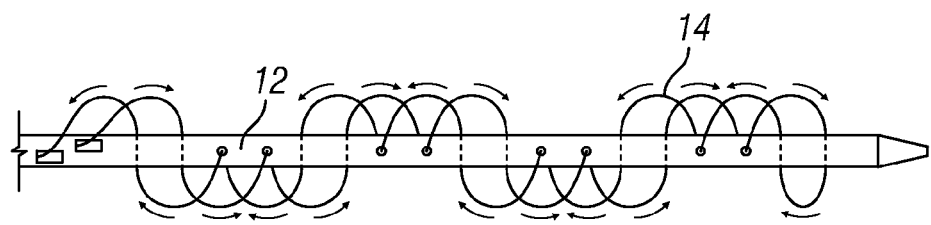
Figure 8D:
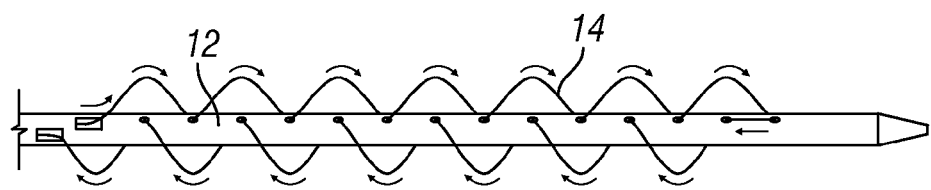
Figure 8E:
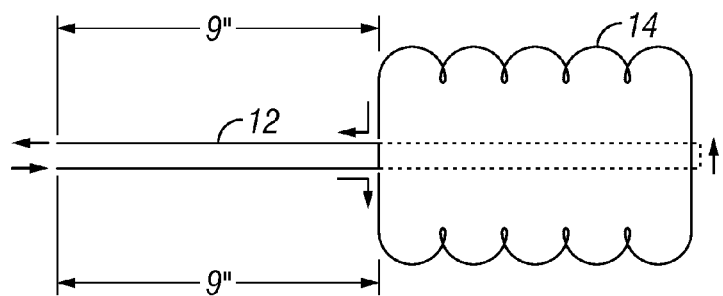
Figure 8F:
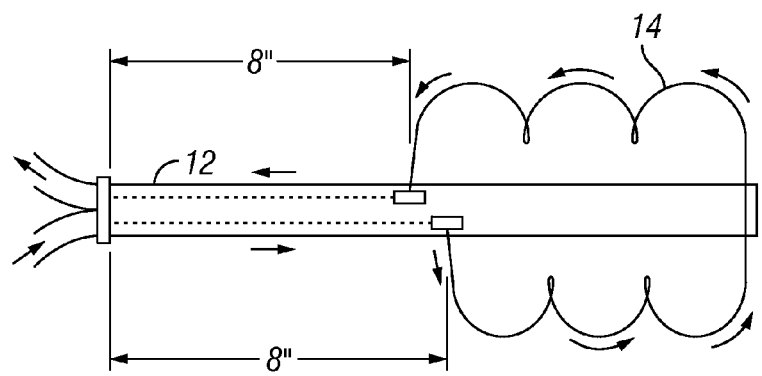
Figure 8G:
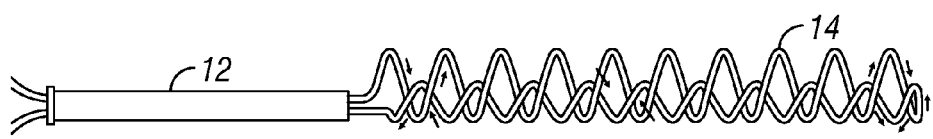

In any embodiments of the invention, the tubular conduit(s) 14, 62 that form the heat exchange region need not necessarily be laced or passed through transverse bores in the catheter shaft 12, as in the above described examples. Rather, in some embodiments, the heat exchange region 60 may be disposed on the exterior of, or may be apart from, the catheter shaft and only the inlet and outlet ends of the supply and return flow paths need be connected to the catheter shaft so as to receive and exhaust circulating heat exchange medium from the inflow and return lumens of the catheter shaft. Also, as explained above, the tubular conduit(s) that form the supply and return flow paths may be coiled of looped in various shapes or configurations. FIGS. 8A through 8G show a series of non-exhaustive, non-limiting examples of alternative designs and configurations that are possible in accordance with the present invention. In FIG. 8A, the tubular conduit 14 is passed through bores in the catheter shaft 12 in different transverse planes to form generally sinusoidal loops that protrude in different planes from the catheter shaft 12. In FIG. 8B, the tubular conduit 14 is passed through bores formed in the catheter body to form a helix with the supply and return flow paths passing through alternating side by side convolutions of the helix. In FIG. 8C the tubular conduit 14 is laced through grouped bores in the catheter shaft 12 in a double cloverleaf pattern, as shown. In FIG. 8D the tubular conduit 14 is passed through bores in the catheter shaft 12 such that separate helical supply and return flow paths are formed. In FIG. 8E, the tubular conduit 14 is not passed or laced through bores in the catheter shaft 12 but, rather, is formed in separate coiled supply and return flow paths which are connected to inflow and outflow lumens of the catheter and which protrudes beyond the distal end of the catheter shaft. Optionally, as indicated by dotted lines on FIG. 12, the catheter shaft could extend to or beyond the distal end of the heat exchange region formed by the tubular conduit 14 and the tubular conduit 14 could optionally be mounted on or supported by such distal extension of the catheter shaft 12. FIG. 8F shows a configuration similar to that of FIG. 8E but wherein the tubular conduit 14 passes through the interior of the catheter shaft 12 thereby itself forming inflow and outflow lumens through the proximal catheter shaft 12. Although the examples of FIGS. 8A through 8F show the return and supply portions of the tubular conduit 14 being coiled in loops of substantially the same size, it is to be appreciated that the loops may differ in size. For example, the loops of the return flow path may be smaller in diameter or cross-dimension that those of the supply flow path or vice versa and/or the actual length of the tubular conduit forming the return flow path may be shorter than that which forms the supply flow path or vice versa. Varying size of the loops in the supply and return flow paths is again illustrated by the additional non-limiting example of FIG. 8G. In the example of FIG. 8G, a tubular conduit 14 that is substantially the same as that shown in FIG. 5 is attached to and extends distally from a catheter shaft 12 thereby forming a catheter device having a heat exchange region on the distal end of the catheter wherein the heat exchange region comprises a coiled supply flow path and a coiled return flow path with the supply flow path being coiled in loops that are larger in diameter or cross-dimension than the coiled loops of the return flow path. Also, in the embodiment of FIG. 8G, the length of the tubing 14 forming the return flow path 14 is shorter than the length of the tubing 14 that forms the supply flow path.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A method for modifying or controlling a body temperature in a mammalian subject, said method comprising the steps of:
   inserting, into the vasculature of the subject, a heat exchange catheter which comprises an elongate catheter shaft having an inflow lumen, an outflow lumen and a heat exchange region, wherein the heat exchange region comprises a tubular conduit, one end of said tubular conduit being connected to the heat exchange catheter's inflow lumen and the other end of said tubular conduit being connected to the heat exchange catheter's outflow lumen, a first segment of the tubular conduit having loops or convolutions of a first diameter or cross-dimension, said first segment forming a fluid supply flow path through which heat exchange fluid may flow in a distal direction from an end of the tubular conduit that is connected to the catheter inflow lumen and a second segment of the tubular conduit having loops or convolutions of a second diameter or cross-dimension, said second segment forming a fluid return flow path through which heat exchange fluid may return in a proximal direction to an end of the tubular conduit that is connected to the catheter's outflow lumen, wherein one of said first and second diameters or cross-dimensions is larger than the other of said first and second diameters or cross-dimensions;
   causing the heat exchange region to be positioned in contact with blood flowing through the subject's vasculature; and
   causing a heat exchange fluid to circulate in a distal direction through the inflow lumen, then through the loops or convolutions of the first diameter or cross-dimension of the fluid supply flow path and then in a proximal direction through the loops or convolutions of the second diameter or cross-dimension of the fluid return flow path, and then through the outflow lumen.

2. A method according to claim 1 wherein the fluid supply flow path has loops or convolutions which overlap or cross loops or convolutions of the fluid return flow path.

3. A method according to claim 1 wherein the fluid supply flow path differs in length from the fluid return flow path.

4. A method according to claim 1 wherein the heat exchange catheter is connected to an apparatus which circulates heated or cooled heat exchange fluid through the heat exchange catheter while in use.

5. A method according to claim 4 further comprising the steps of:
   using a temperature sensor to sense a subject body temperature; and
   adjusting the temperature or flow rate of the heat exchange fluid as needed to cause the body temperature sensed by the temperature sensor to be within a desired range of a target temperature.

6. A method according to claim 5 wherein the temperature sensor is connected to a controller, said controller being programmed to adjust the temperature or flow rate of the heat exchange fluid in response to indications of the sensed subject body temperature that the controller receives from the temperature sensor.

7. A method according to claim 6 further comprising inputting a target body temperature to the controller.

8. A method according to claim 1 wherein the first and second flow paths comprise one or more tubes which a) are in a collapsed configuration during the step of inserting the heat exchange catheter and b) assume an expanded configuration when heat exchange fluid is subsequently circulated therethrough.

9. A method according to claim 1 wherein the tubular conduit has a wall thickness of less than 0.001 inch and withstands pressures of up to approximately 100 psi when the heat exchange fluid is being circulated.

10. A method according to claim 1 wherein the tubular conduit has a wall thickness that is thinner than the wall thickness of the catheter shaft.

11. A method according to claim 1 wherein the tubular conduit is laced or passed through passageways in a distal portion of the catheter shaft.

12. A method according to claim 1 wherein the catheter has a through lumen that terminates distally in a distal port.

13. A method according to claim 12 wherein the through lumen is used as a guidewire lumen to facilitate insertion of the catheter over a guidewire.

14. A method according to claim 12 wherein the through lumen is used as a delivery lumen to facilitate delivery of a therapeutic substance or device.

15. A method according to claim 1 wherein loops or convolutions formed in the fluid supply flow path are not coaxial with loops or convolutions in the fluid return flowpath.

16. A method according to claim 1 wherein loops or convolutions formed in the fluid supply flow path are coaxial with loops or convolutions formed in the fluid return flowpath.

17. A method according to claim 1 wherein the tubular conduit is not laced or passed through the catheter shaft.

18. A method according to claim 1 wherein the tubular conduit is laced or passed through transverse passages in the catheter shaft.

* * * * *